(12) United States Patent
Djurovic

(10) Patent No.: US 10,213,196 B2
(45) Date of Patent: Feb. 26, 2019

(54) REVERSIBLE SURGICAL SUTURING DEVICE

(71) Applicant: Zarija Djurovic, Chicago, IL (US)

(72) Inventor: Zarija Djurovic, Chicago, IL (US)

( * ) Notice: Subject to any disclaimer, the term of this patent is extended or adjusted under 35 U.S.C. 154(b) by 387 days.

(21) Appl. No.: 14/577,207

(22) Filed: Dec. 19, 2014

(65) Prior Publication Data

US 2016/0174966 A1    Jun. 23, 2016

(51) Int. Cl.
*A61B 17/12* (2006.01)
*A61B 17/04* (2006.01)
*A61B 17/06* (2006.01)

(52) U.S. Cl.
CPC .... *A61B 17/0469* (2013.01); *A61B 17/06066* (2013.01); *A61B 17/0491* (2013.01); *A61B 17/06123* (2013.01); *A61B 17/0498* (2013.01); *A61B 2017/06052* (2013.01); *A61B 2017/06076* (2013.01)

(58) Field of Classification Search
CPC ............ A61B 17/0469; A61B 17/0496; A61B 17/06114; A61B 17/06119; A61B 17/06123; A61B 17/06128; A61B 2017/06052; A61B 2017/06076
See application file for complete search history.

(56) References Cited

U.S. PATENT DOCUMENTS

| | | | | |
|---|---|---|---|---|
| 6,221,085 B1 * | 4/2001 | Djurovic | ............ | A61B 17/0469 606/144 |
| 6,253,774 B1 * | 7/2001 | Mason | ................. | A61C 15/046 132/325 |
| 6,280,441 B1 * | 8/2001 | Ryan | ..................... | A61B 18/148 600/373 |
| 6,315,784 B1 * | 11/2001 | Djurovic | .......... | A61B 17/06109 606/146 |
| 7,862,582 B2 * | 1/2011 | Ortiz | .................. | A61B 17/0483 242/375 |
| 2010/0318105 A1 * | 12/2010 | Jayant | .............. | A61B 17/12013 606/148 |
| 2012/0143226 A1 * | 6/2012 | Belson | ............... | A61B 17/0057 606/148 |
| 2012/0165837 A1 * | 6/2012 | Belman | .............. | A61B 17/0469 606/144 |
| 2015/0289867 A1 * | 10/2015 | Najar | ................. | A61B 17/0469 606/144 |

* cited by examiner

*Primary Examiner* — Katrina Stransky
*Assistant Examiner* — Martin T Ton
(74) *Attorney, Agent, or Firm* — Clifford H. Kraft

(57) ABSTRACT

A hand-held, surgical suturing device that can be operated and manipulated with one hand. The device has a suture spool that can be locked The device can rotate in either direction. It is configured to accept at least two different types of needles, a single hook needle and a corkscrew needle useful in different suturing applications. These needles can be supplied in different sizes and shapes. The needle, suture spool and needle carrier are typically supplied in sterile packages and are disposable. A first embodiment has a triangular-shaped squeeze handle that, when squeezed, causes the needle to rotate. A second embodiment has a cylindrical handle for manual stitching where the needle can be released to freely rotate by pressing a control button. In either embodiment, the suture spool can be locked or allowed to rotate freely by activating a releasing rod.

11 Claims, 8 Drawing Sheets

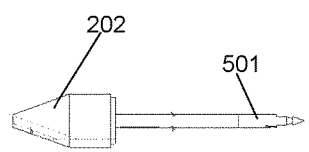
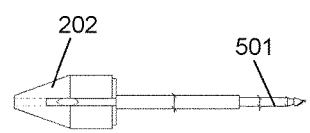
FIG. 8A　　　　　　　　　　　　　FIG. 8B
   
FIG. 9A　　FIG. 9B　　FIG. 10A　　FIG. 10B

REVERSIBLE SURGICAL SUTURING DEVICE

BACKGROUND

Field of the Invention

The present invention relates generally to suturing devices used in surgery, especially laparoscopic surgery and more particularly to an improved reversible hand-controlled suturing device.

Description of the Prior Art

Suturing is a necessary part of most surgeries. Surgeons need to be able to continuously suture different types of tissues using a device that can store large amounts of different suturing materials. There are prior art suturing devices that allow both suturing and the storing of suturing material; however, these devices can only be used to suture in one direction. Among these prior art devices are my inventions disclosed in U.S. Pat. Nos. 6,221,085 and 6,315,784. It would be tremendously advantageous to have a hand-powered and controlled surgical suturing device that takes disposable sterile needles of two different types, for left turn and right turn suturing, for storing the suturing material internally, and which is easily manipulated with one hand.

SUMMARY OF THE INVENTION

The present invention relates to a hand-held, surgical suturing device that can be operated and manipulated with one hand. The device can lock the spool in order to prevent the unnecessary release of suture material. The device can also use a suture unit containing a curved needle for either right or left turn suturing. Shape wise, the needle can be either single hook or curved for placement of an interrupted stitch, or a multi-coiled needle that can place continuous stitching in the length related to the number of coils. These needles can be supplied in different sizes and preloaded with different suture material.

Embodiments of the present invention include an elongated hollow shaft with an internal rotatable drive rod. A smaller locking rod also runs inside the hollow shaft. A removable needle carrier fits onto the distal end of the rotatable drive rod. This needle carrier includes a conical cap part that receives the needle at its apex, and an extended cylindrical part that holds a spool of suturing material. The proximal end of the spool is made with teeth in between which a spool locking rod can be engaged in order to prevent unwanted release of suture material.

At the proximal end of the elongated hollow shaft, a particular embodiment of the invention includes a triangular shaped arrangement of two handles, one moving and the other stationary. When the surgeon squeezes the handles together, a linear gear arrangement causes the drive rod to turn the suture unit which is attached to the distal end. This, in turn, causes the needle to rotate with the suture material. The surgeon can then tie the knot in the sutures. The linear gear arrangement in the handle includes a control that can reverse the direction of rotation.

An alternate embodiment of the invention includes a cylindrical handle instead of a triangular squeeze drive. In this embodiment, the surgeon can allow the spool to spin as the locking rod is retracted allowing the release of a desired amount of suture material; then, when the surgeon releases pressure on a locking rod control button, a spring pushes the locking rod toward the distal end of the hollow shaft to engage the spool tooth gear to lock the spool. The surgeon can then tie the stitch.

DESCRIPTION OF THE FIGURES

Attention is now directed to several figures that illustrate features of the present invention.

FIG. 8A shows a side view of the needle carrier.

FIG. 8B shows a section of the needle carrier of FIG. 8A.

FIGS. 9A-9B show a right and left handed curved needle.

FIGS. 10A-10B show a right and left handed corkscrew needle.

Several drawings and illustrations have been presented to aid in understanding the present invention. The scope of the present invention is not limited to what is shown in the figures.

DESCRIPTION OF THE PREFERRED EMBODIMENTS

Figure 1:
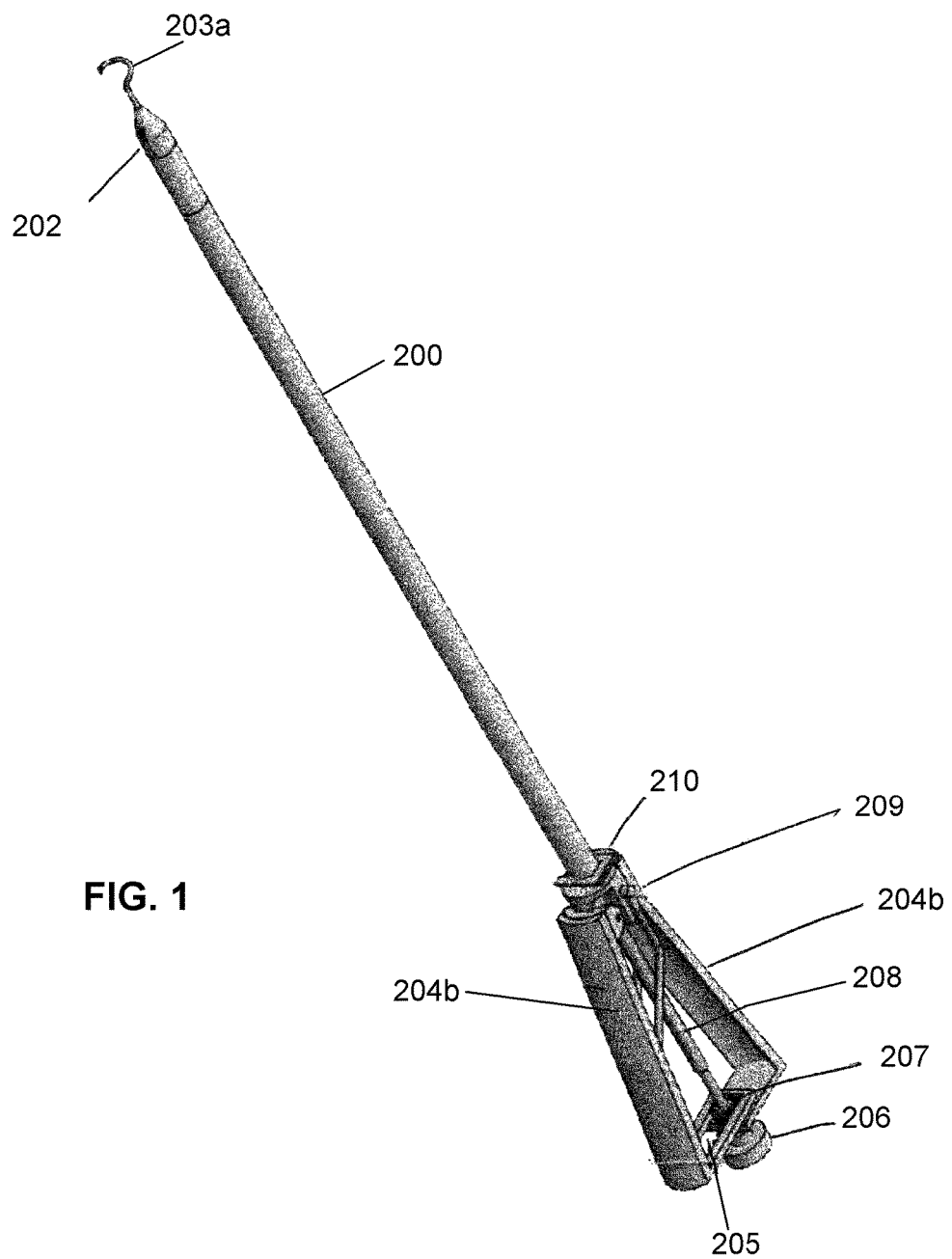
FIG. 1 shows an embodiment of the present invention with a squeeze handle.

The present invention relates to an improved, hand-held, hand-controlled, reversible surgical suturing device. FIG. 1 shows an embodiment of the invention. An elongated hollow shaft 200 attaches to a suture material spool compartment 201 on a distal end of the shaft 200 that, in turn, attaches to a needle carrier 202 that is configured to receive a suturing needle 203a. The suturing needle is hollow, and suture can be threaded through the needle from a spool. FIG. 1 shows a curved suturing needle; however, the needle may also be of a corkscrew configuration or any other configuration. Also the needle 203 may be curved right handed or left handed.

At the proximal end of the hollow shaft 200, there is a triangular arrangement of two squeeze handles 204a and 204b. one fixed and the other able to move inward when squeezed. These squeeze handles drive a rotatable shaft 208 that extends into, and runs the length of, the hollow shaft 200 that causes the needle carrier 202 and the needle 203a to rotate when the handles 204a and 204b are squeezed together. A linear gear arrangement 205 engages a circular drive shaft end gear 207 on the end of the drive shaft 208 that causes the drive shaft 208 to rotate. A control button 206 allows both release of the needle carrier from the shaft 200 by means of a set of internal jaws. The circular gear can engage either one side of the linear gear 205 thus allowing the surgeon to reverse the direction of rotation by changing which side of the linear gear is engaged.

A locking button 209 moves a locking rod (shown in FIG. 3) that extends inside the hollow shaft 200 in or out of the suture spool to cause the spool to lock and not rotate. This prevents unwanted extra suture from unraveling from the spool. The locking button and rod are spring-biased so that the spool is locked in the default condition. To disassemble the unit for cleaning, the control 206 is released, and the entire needle carrier 202, suture compartment 201 and needle 203a or 203b is removed as a disposable suturing unit. A C-clip 210, or other fastening device, can be removed releasing the hollow shaft 200 from the handle. The hollow shaft 200 can simply be a piece of tubing which can be pulled off. This exposes the drive shaft 208 and the locking rod 400 (shown in FIG. 3). All of the components can be soaked using approved surgical cleaning methods. The instrument can be reassembled by sliding the hollow shaft 200 over the drive shaft 208 and the locking rod 400. The tip of the hollow shaft 200 can have a cover with a larger hole for the drive shaft 208 and a smaller peripheral hole for the locking rod 400. The proximal end of the hollow shaft 200 can contain a small slat that engages one or more slots on the handle. The C-clip 210 can then be inserted at the proximal end of the shaft 200 to lock it to the handle. A new pre-sterilized suturing unit with suture, and needle can then be attached to the hollow shaft 200 by releasing the control button 206, inserting the needle carrier and suture compartment combination 202, 201, and releasing the button 206.

Figure 2:
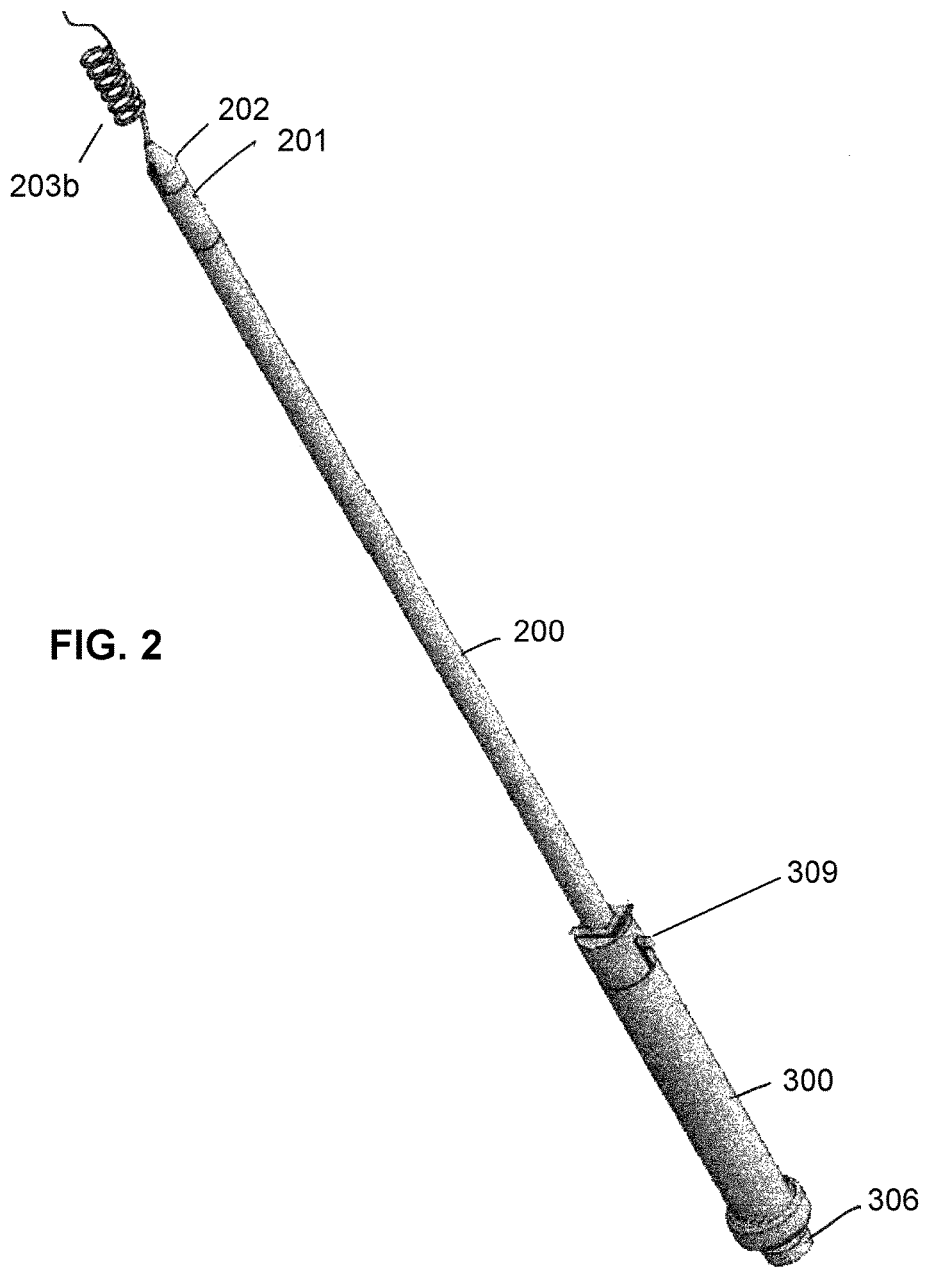
FIG. 2 shows an alternate embodiment of the present invention with a cylindrical handle.

FIG. 2 shows an alternate embodiment of the present invention. In this embodiment, the distal and central part of the hollow shaft 200, the spool compartment 201 and the needle carrier 202 are similar to the embodiment of FIG. 1. However, the proximal end of the hollow shaft 200 terminates in a cylindrical handle 300 that can be manipulated manually. A locking rod button 309 is located at the top of the cylindrical handle 300 that engages the locking rod (shown in FIG. 3) causing the suture spool to lock. In this embodiment, the surgeon engages the locking rod button 309 to pull the locking rod down on its spring to take out a desired amount of suture material, and then releases the locking rod button 309. The spring (shown in FIG. 7) inside the cylindrical handle 300 forces the locking rod back into a locked position allowing suturing. A release control knob 306 can be seen on the bottom of the proximal end of the device. This is used to release the internal jaws and remove the needle carrier 202. FIG. 2 shows a corkscrew needle 203b. The present invention can accept any type of removable needle. The corkscrew needle 203b is more useful with the manual embodiment of FIG. 2.

Figure 3:
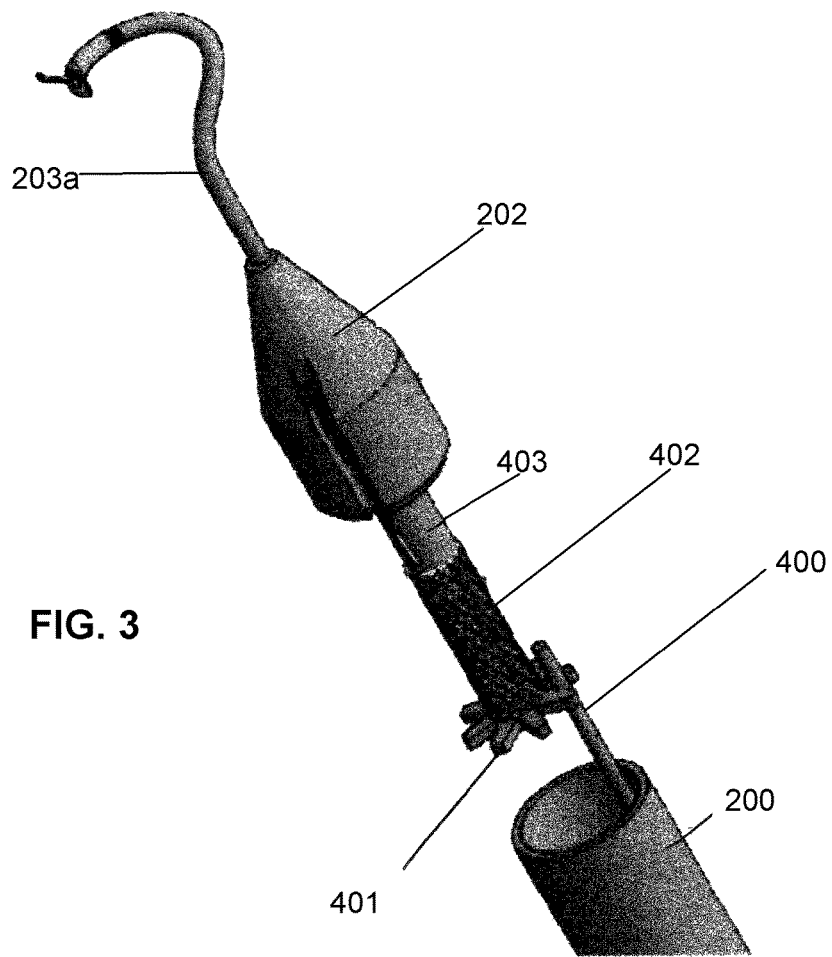
FIG. 3 shows the distal end of various embodiments of the invention including the needle carrier, locking rod and curved needle.
Figure 4:
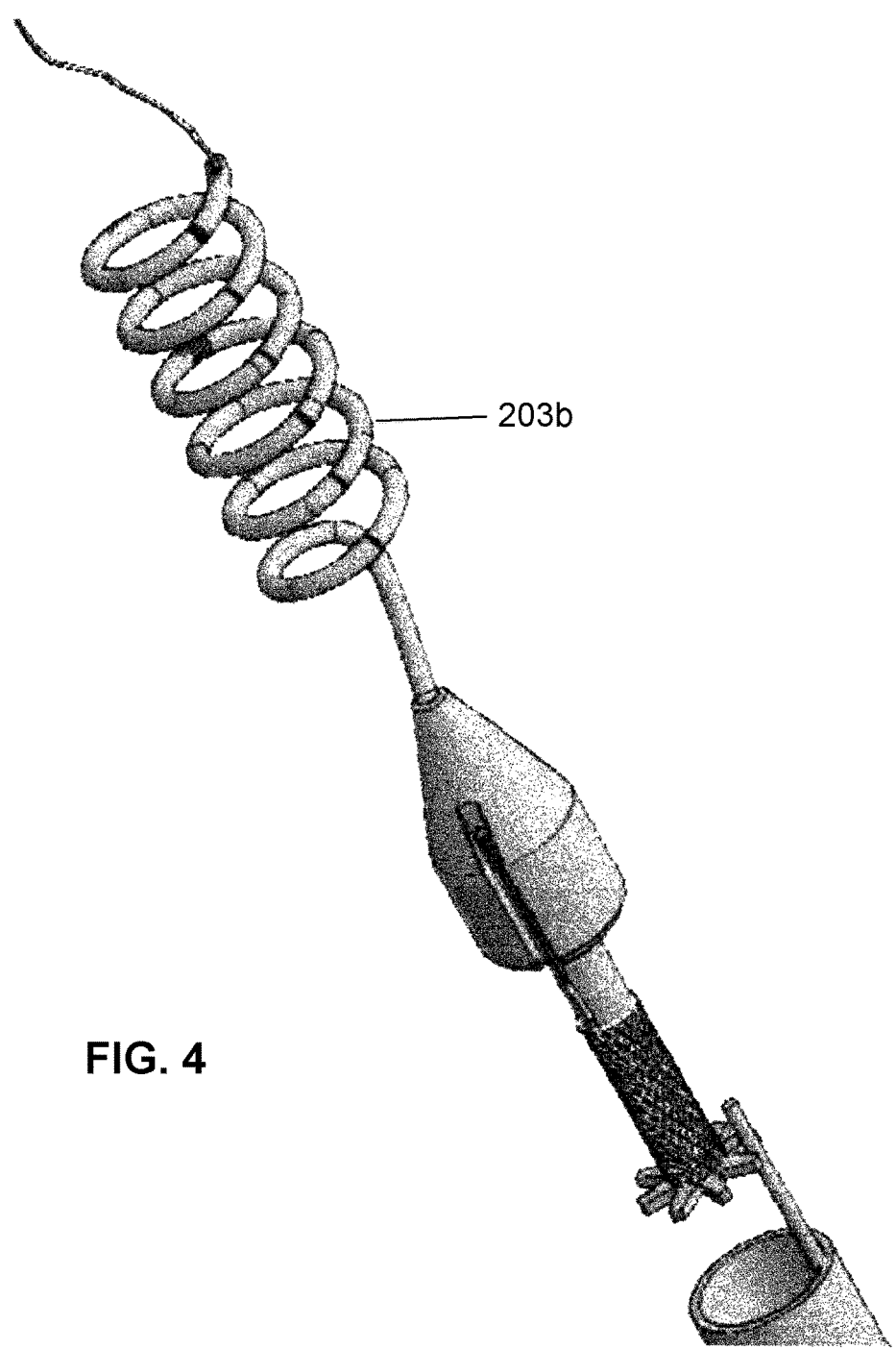
FIG. 4 shows the distal end of various embodiments of the invention including the needle carrier locking rod and corkscrew needle.

FIGS. 3-4 show details of the distal end of embodiments of the present invention. FIG. 3 shows a curved needle 203a, while FIG. 4 shows a corkscrew needle 203b. The needle carrier 202 is configured to receive a removable, sterile needle 203a (or 203b from FIG. 4). The needle 203a locks into the needle carrier 202 and is typically supplied with it as a disposable unit. The lower end of the needle carrier 403 is cylindrical and is configured to receive a spool 402 of suturing material. The suturing material can be Silk 2-0, 3-0, chromic 2-0, 3-0, polyester 2-0, 3-0 and nylon 2-0, 3-0. While these are the common suturing materials, any suturing material may be used with the present invention. The sterile suture is also usually supplied with the needle carrier as a single disposable unit. Below the cylindrical portion 403 of the needle carrier is a locking gear 401 having protruding teeth. The locking gear is part of the suture spool 402. A locking rod 400 that extends the length of the hollow shaft 200 can be moved toward and away from the distal end of the device. When the locking rod 400 is moved toward the distal end, it engages the teeth in the locking gear 401 causing the spool 402 to lock in position and not rotate. When the locking rod is moved away from the distal end of the device, it releases the locking gear 401 allowing the spool 402 to rotate either freely.

Figure 5B:
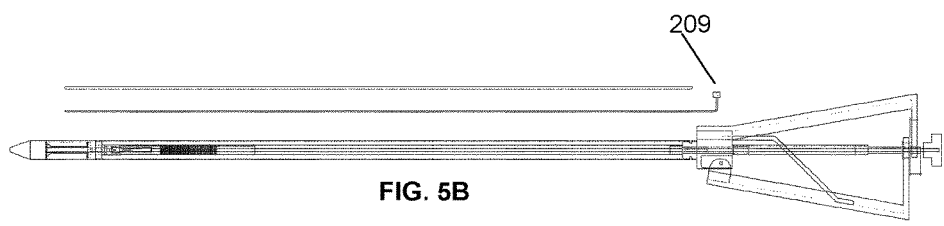
FIG. 5B shows a sectional view of the assembled squeeze-handle embodiment.
Figure 5A:
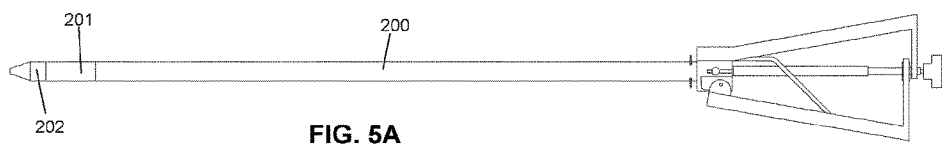
FIG. 5A shows a side view of the assembled squeeze-handle embodiment.

FIGS. 5A-5B show side views of the embodiment of FIG. 1. FIG. 5A is a simple side view of the assembled device, while FIG. 5B is a sectional view. The elongated hollow shaft 200 terminates in the spool compartment 201 and the needle carrier 202. At the proximal end, the hollow shaft 200 terminates at the juncture of the two squeeze handles 204a and 204b. The drive shaft 208, and locking shaft button 209 can be seen. The jaw release 206 is used to release the spool compartment and needle and allow replacement with a new sterile assembly.

Figure 6A:
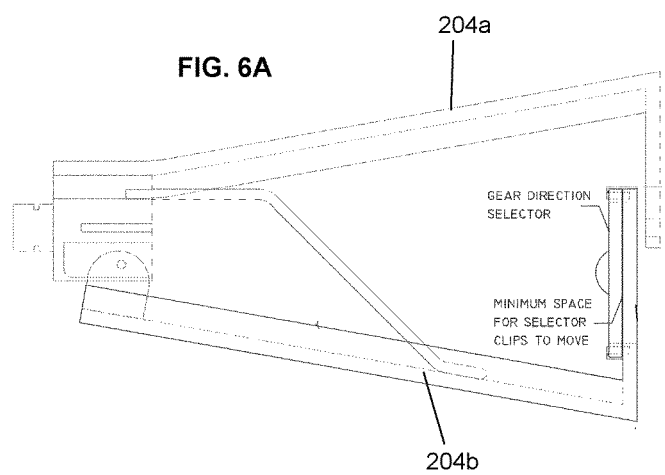
FIG. 6A shows a detail view of the triangular-shaped handle.
Figure 6B:
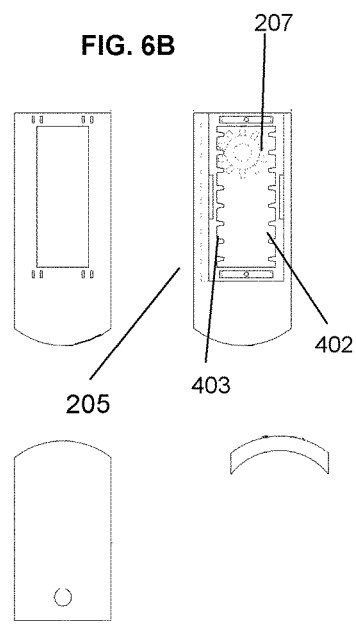
FIG. 6B shows details of the linear gear arrangement.

FIG. 6A shows details of the triangular-shaped squeeze handle including the left 204a fixed handle and right 204b handle squeezable members and the linear gear 205. FIG. 6B shows details of the linear gear 205 and shaft end gear 207. The linear gear 205 includes two tracks, a left track 402 and a right track 403. The gear 207 only engages one of the left track 402 or the right track 403 at a time. The direction of rotation of the drive shaft 208 when the handles 204a and 204b are squeezed together and hence the direction of rotation of the suturing needle is determined by whether the left 402 or right 403 track is engaged.

Figures 7A, 7B:
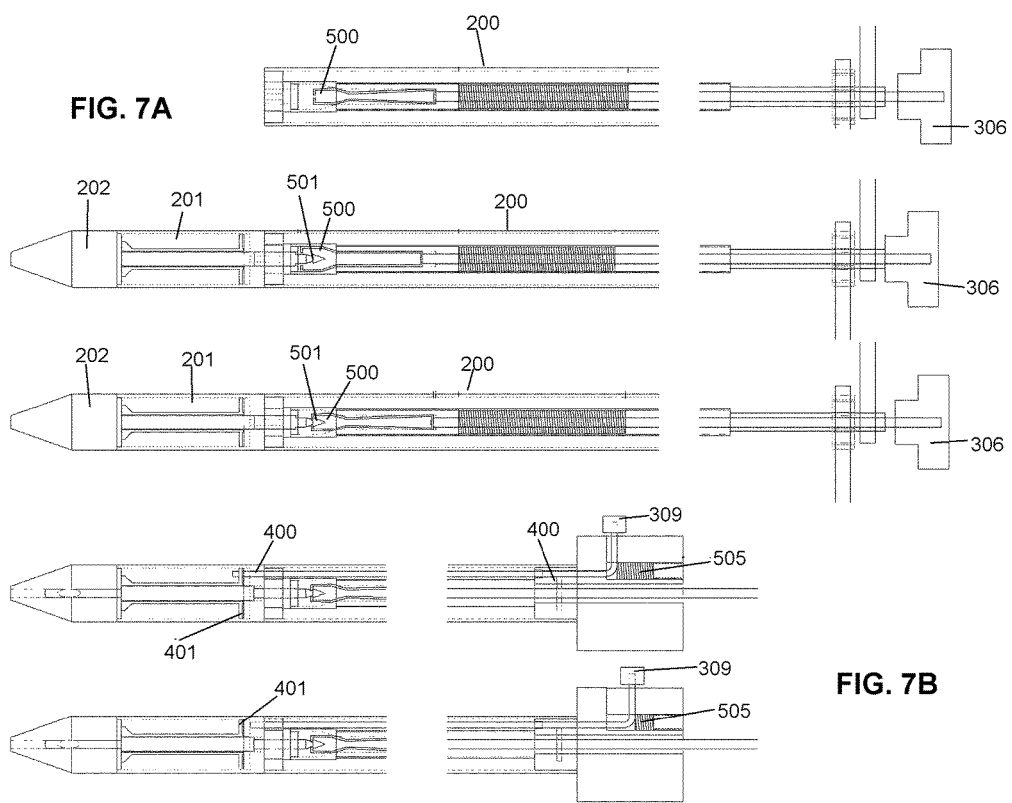
FIG. 7A shows details of the cylindrical-handle embodiment including the mechanism the releases the needle carrier.
FIG. 7B shows details of the operation of the locking rod and its associated spring.

FIG. 7A shows details of the embodiment of FIG. 2. The top drawing shows a needle carrier clamp 500 located inside the hollow shaft 200 in a relaxed position with no needle carrier. The second drawing shows the clamp 500 extended into an open or receiving position by adjustment of the release control 306. The clamp jaw 500 receives the end shaft 501 as the needle carrier 202 and suture compartment 201 are loaded. The release control 306 is then relaxed to a locked position causing the clamp jaw 500 to lock down on the end shaft 501 securing the needle carrier 202 to the hollow shaft 200. In a particular example shown in FIG. 7A, the release control 306 is 0.0840 inches from its bottom position in a relaxed configuration, 0.0000 inches at the bottom or open position, and 0.0675 inches from the bottom position in the locked configuration. These dimensions and numbers are given to aid in understanding the operation of the clamp jaw 500. Any distances, dimensions or numbers may be used.

FIG. 7B shows the operation of the locking rod 400. The locking rod button 309 can be moved toward or away from the distal end of the device. A spring 505 engages the locking rod 400 and biases it into the locked position. When the surgeon desires to release the spool to draw out suture, the locking rod button 309 is moved toward the proximal end of the device compressing the spring 505 as shown in the lower drawing of FIG. 7B. The locking rod 400 disengages from the locking gear 401 on the spool 402 (details shown in FIGS. 3-4). When the surgeon has drawn out enough suture and desires to stitch, the locking rod button 309 is released. The spring 505 pushes the locking rod 400 toward the distal end of the device, and it engages between two teeth in the locking gear 401. This locks the spool 402.

FIG. 8A is a side view of the needle carrier 202, while FIG. 8B is a sectional view. The end of the needle carrier shaft 501 is configured so that it can be received and clamped into the device by the clamp jaw 500 shown in FIG. 7A.

FIGS. 9A-9B show a left and right-handed configuration of a curved needle. The curved needle is preferred for use with the squeeze embodiment of FIG. 1. FIGS. 10A-10B show a left and right-handed configuration of a corkscrew needle. The corkscrew needle is preferred for use with the embodiment of FIG. 2. However, any needle of any type may be used with either of the embodiments of the present invention.

In various embodiments of the present invention, components may be made of convenient materials including metal and plastic. The needle carrier may be made of plastic using silicone epoxy to hold the needle. Alternatively, the needle carrier may be made of stainless steel with the needle attachment being silver soldered.

Several descriptions and drawings have been presented to aid in understanding the present invention. One with skill in the art will realize that numerous changes and variations may be made without departing from the spirit of the invention. Each of these changes and variations is within the scope of the present invention.

I claim:

1. A surgical suturing device comprising:
a tubular elongated hollow shaft having a distal and proximal end, the hollow shaft configured to receive and engage on its distal end a removable needle carrier with a hollow curved or corkscrew needle fixed to the needle carrier the needle carrier being attached to a suture compartment adapted to receive and hold a suture spool such that suture can be threaded and fed from the spool through the hollow needle;
the elongated hollow shaft containing an internal drive shaft adapted to engage and rotate the needle carrier, the hollow shaft also containing a locking rod adapted to lock the suture spool in a fixed rotational position, the locking rod having a locked configuration where the suture spool is prevented from rotating, and an unlocked configuration where the suture spool is allowed to rotate;
a squeeze handle removably attached to the proximal end of the elongated hollow shaft, the squeeze handle configured to engage the proximal end of the drive shaft allowing the needle carrier to rotate in a chosen direction in response to squeezing the squeeze handle;
first and second separated adjacent parallel linear gear tracks attached to the squeeze handle cooperating with a circular gear located between the tracks, the tracks switchably configured so that only one of the tracks engages the circular gear, the circular gear attached to the proximal end of the drive shaft, wherein when the squeeze handle is squeezed, the linear gears move in relation to the circular gear causing the circular gear and the drive shaft to rotate;
a switch that changes which track engages the circular gear, the switch controlling direction of rotation of the drive shaft;
wherein the needle carrier, suture spool, suture compartment and needle comprise a single integral, sterile disposable unit independent of the elongated hollow shaft and removable from it; wherein the single integral, sterile disposable unit is disposed of after use and replaced by a new integral, sterile disposable unit for a next use.

2. The surgical suturing device of claim 1 wherein the drive shaft is centrally located in the elongated hollow shaft.

3. The surgical suturing device of claim 1 wherein the locking rod is located off-center in the elongated hollow shaft.

4. The surgical suturing device of claim 1 wherein the locking rod engages a toothed gear fixedly attached to the suture spool in the locked configuration.

5. The surgical suturing device of claim 1 wherein the squeeze handle comprises a pair of flat handle members configured in a triangle.

6. The surgical suturing device of claim 1 wherein the needle carrier has a protruding engagement shaft on its proximal end that mates into a clamp jaw on the drive shaft, the clamp jaw being releasable by engaging a control located on the squeeze handle.

7. The surgical suturing device of claim 1 wherein the locking rod is controlled with a protrusion on the squeeze handle that allows it to move toward or away from the distal end of the hollow shaft.

8. The surgical suturing device of claim 1 wherein the needle is curved.

9. The surgical suturing device of claim 1 wherein the needle is corkscrew-shaped.

10. A surgical suturing device comprising:
a tubular elongated hollow shaft having a distal and proximal end, the hollow shaft configured to receive and engage on its distal end a removable needle carrier with a hollow curved or corkscrew needle fixed to the needle carrier the needle carrier being attached to a suture compartment adapted to receive and hold a suture spool such that suture can be threaded and fed from the spool through the hollow needle;
the elongated hollow shaft containing an internal drive shaft adapted to engage and rotate the needle carrier, the hollow shaft also containing a locking rod adapted to lock the suture spool in a fixed rotational position, the locking rod having a locked configuration where the suture spool is prevented from rotating, and an unlocked configuration where the suture spool is allowed to rotate;
a squeeze handle removably attached to the proximal end of the elongated hollow shaft, the squeeze handle configured to engage the proximal end of the drive shaft allowing the needle carrier to rotate in a chosen direction in response to squeezing the squeeze handle;
first and second separated adjacent parallel linear gear tracks attached to the squeeze handle cooperating with a circular gear located between the tracks, the tracks switchably configured so that only one of the tracks engages the circular gear, the circular gear attached to the proximal end of the drive shaft, wherein when the squeeze handle is squeezed, the linear gears move in relation to the circular gear causing the circular gear and the drive shaft to rotate.

11. The surgical suturing device of claim 10 wherein the needle carrier, suture spool, suture compartment and needle comprise a single integral, sterile disposable unit independent of the elongated hollow shaft and removable from it; wherein the single integral, sterile disposable unit is disposed of after use and replaced by a new integral, sterile disposable unit for a next use.

* * * * *